United States Patent
Cianfarani

(10) Patent No.: US 7,087,587 B2
(45) Date of Patent: Aug. 8, 2006

(54) PROCESS FOR THE PREPARATION OF TABLETS COMPRISING S-ADENOSYLMETHIONINE

(75) Inventor: Giuseppe Cianfarani, Sora (IT)

(73) Assignee: Gnosis SRL, Cairate (IT)

( * ) Notice: Subject to any disclaimer, the term of this patent is extended or adjusted under 35 U.S.C. 154(b) by 126 days.

(21) Appl. No.: 10/490,376

(22) PCT Filed: Oct. 18, 2002

(86) PCT No.: PCT/EP02/11680

§ 371 (c)(1),
(2), (4) Date: Apr. 1, 2004

(87) PCT Pub. No.: WO03/043608

PCT Pub. Date: May 30, 2003

(65) Prior Publication Data

US 2004/0248843 A1  Dec. 9, 2004

(30) Foreign Application Priority Data

Nov. 22, 2001 (IT) .......................... MI2001A2462

(51) Int. Cl.
*A61K 31/7076* (2006.01)
*B27N 3/00* (2006.01)

(52) U.S. Cl. ........................................ 514/46; 264/109
(58) Field of Classification Search .................. 514/46; 264/109
See application file for complete search history.

(56) References Cited

U.S. PATENT DOCUMENTS 4,028,183 A    6/1977  Fiecchi
6,117,849 A *  9/2000  Zimmermann et al. ....... 514/45

FOREIGN PATENT DOCUMENTS

| EP | 0084169 |   | 7/1983 |
| EP | 0387756 |   | 9/1990 |
| EP | 0482493 | * | 4/1992 |
| KR | 2001045285 |   | 6/2001 |
| WO | 0126646 |   | 4/1901 |
| WO | 0012071 |   | 3/2000 |

* cited by examiner

*Primary Examiner*—Shaojia A. Jiang
*Assistant Examiner*—Ganapathy Krishnan
(74) *Attorney, Agent, or Firm*—Oblon, Spivak, McClelland, Maier & Neustadt, P.C.

(57) ABSTRACT

The present invention provides a process for the preparation of tablets comprising S-adenosylmethionine and/or a pharmaceutically and/or dietarily acceptable derivative thereof by blending that active component with specified additives, compressing the blend, followed by coating.

14 Claims, No Drawings

PROCESS FOR THE PREPARATION OF TABLETS COMPRISING S-ADENOSYLMETHIONINE

The present invention relates to a process for the preparation of tablets comprising S-adenosylmethionine. Particularly, this invention relates to a process for the preparation of stable tablets comprising S-adenosylmethionine and/or a pharmaceutically and/or dietarily acceptable derivatives thereof.

It is well known that S-adenosylmethionine (hereinafter "SAMe" or the "active ingredient") is a compound endowed with a poor stability at a temperature higher than 0° C. and, accordingly, the pharmaceutical and/or dietary compositions comprising it, reflect such poor stability, this having plain negative effects, on their preservation and storage, also for short periods of time.

U.S. Pat. No. 3,954,726 and U.S. Pat. No. 4,057,686 describe salts of SAMe somewhat stable, at a temperature up to 25° C. and 45° C., respectively.

U.S. Pat. No. 4,465,672 also describes stable salts of SAMe, among which the sulfate p-toluensulfonate, with 5 moles of an organic sulfonic acid having a pK lower than 2.5 together with a process for the preparation of compositions comprising such salts; the process involves the preparation of a concentrated aqueous solution of one of the mentioned raw salts of SAMe, the purification of this solution and its elution through a diluted aqueous solution of the selected sulfonic acid, the titration of the resulting eluate, its concentration and lyophilization.

Due to the high unstability of SAMe and the derivatives thereof, an aqueous environment would show the limits of this process which, although initially succeeding in maintaining the residual humidity, is inadequate in maintaining the initial starting stability of the SAMe salts in oral solid formulations, because of the high hygroscopicity thereof.

U.S. Pat. No. 6,093,703 either, which discloses the usefulness of pharmaceutical compounds comprising at least one active ingredient, among which SAMe, in the treatment of neurological complications in patients suffering from AIDS, describes compositions based on SAMe salts such as, for example, disulfate p-toluensulfonate which, although having a residual moisture (K.F.) initially equal to about 2%, result to be unstable in time due to the high hygroscopicity thereof.

The Applicant observed how SAMe and the derivatives thereof, produced according to the described method, result to be however hygroscopic when exposed to the air and therefore unstable in time.

The packaging of the known compositions, comprising SAMe and the derivatives thereof, results to be particularly toilful and expensive due to the high hygroscopicity of the active ingredient, this causing the rapid degradation thereof, unpleasant smells also in the presence of impurity traces; accordingly, substantially anhydrous environments are needed (in fact the tablets are generally packed in aluminium/aluminium blisters).

Also the accidental exposure to atmospheric humidity, inevitably occuring during the industrial processes (f.i. due to microfractures in the blisters wherein tablets are generally contained), and consequently causing the degradation of SAMe and of the derivatives thereof in the known oral formulations, due to their high hygroscopicity, makes evident the need to develop a process enabling the preparation of compositions showing a lower hygroscopicity and therefore a higher stability.

According to a first aspect, this invention describes a process for the preparation of tablets comprising SAMe and/or one of the pharmaceutically and/or dietarily acceptable derivatives thereof, comprising at a relative humidity, at 20° C., lower or equal to 20%, the following steps:

a) blending of the active principle SAMe and/or a pharmaceutically and dietarily acceptable derivative thereof with 1.0–30.0% of calcium sulfate and/or phosphate, 1.0–10.0% of calcium and/or magnesium carbonate, 1.0–15.0% of glycerol behenate and/or palmitostearate and 0.5–5.0% of silica, the amounts being expressed as weight percentages to the weight of SAMe;

b) compression of the mixture resulting from step a);

c) coating of the mixture resulting from step b) by 0.5–2.5% of Biogapress® vegetal and 0.5–2.5% of Labrafac® cc, at a temperature of 35°–45° C., after 10 to 30 minutes at 60–65° C., the amounts being expressed as weight percentages to the total weight of the mixture resulting from step b).

SAMe in the present invention means both the racemic mixture [(S,R)-SAMe] and the single diastereoisomers (RS)-(+)-S-adenosyl-L-methionine [(RS)-(+)-SAMe)] and (SS)-(+)-S adenosyl-L-methionine [(SS)-(+)-SAMe)], also in mixtures different from the racemic one.

According to a preferred embodiment, after the blending step a), the process of the invention comprises:

a') the pre-compression of the mixture resulting from step a); and a") the granulation of the mixture resulting from step a').

Examples of pharmaceutically and dietarily acceptable SAMe derivatives are preferably selected among the salts with the sulfuric acid and/or the p-toluensulfonic acid.

The process of the invention allows to obtain tablets that, though having the same dosage of the active ingredient, with respect to the commercialised tablets such as, for example, Samyr®, are poorly hygroscopic, show a good compressibility, have a low moisture and are stable.

Preferably, in step a), 1.0–30.0% by weight to the SAMe weight of anhydrous microcrystalline is added.

The tablets obtained from step a) are granulated (generally, their dimension being equal to 1200–1600 μm), then compressed, thus obtaining the core of the tablets, which will be then coated by a protective film comprising Biogapress® vegetal and Labrafac®cc.

The process of the invention, according to a further embodiment, comprises the coating of the tablets protected with a gastroresistant film. In particular, this gastroresistant film comprises 1.0–5.0% of Eudragit®, Shellac® and/or at least a water-soluble salt thereof, 1.0–3.0% of titanium dioxide, 1.0–3.0% of talc, 0.1%–1.0% of triethylcitrate and/or glycerine, 0.004–0.04% of ferric oxide, the amounts being expressed as weight percentages to the total weight of the mixture resulting from step b). Shellac® and, in particular, the water-soluble salts thereof are preferred components; a 1:1 mixture of potassium and ammonium salts of Shellac® is particularly preferred.

According to a further preferred aspect, in step a), at least another active ingredient is added, selected among 100–150% of glucosamine sulfate, 80–120% of chondroitin sulfate, 100–150% of methylsulfonylmethane (MSM), 0.1–0.5% of vitamin $B_6$, 0.04–0.2% of vitamin $B_{12}$, 0.03–0.15% of folic acid, the amounts being expressed as weight percentages to the weight of SAMe.

Any excipient mentioned, i.e. all of the above mentioned components but SAMe, the derivatives thereof and the other above mentioned active ingredients, used in the process of the invention, according to a preferred embodiment, including the gastroresistant coating, are all-natural ingredients.

According to a second aspect, the invention describes tablets comprising SAMe and/or one of the pharmaceutically and/or dietarily acceptable derivatives thereof obtainable by the above described process.

The tablets obtainable by the process of the invention comprise, preferably, all-natural components only and undergo an increase in moisture about four time lower than the tablets containing SAMe (for example, those sold by Knoll under the trademark Samyr®).

The following examples illustrate the invention without limiting it.

EXAMPLE 1

In the following tablets, if not otherwise specified, the initials used have the meanings and the units of measure listed below: T=temperature (° C.); t=time (months); R.H.=relative humidity (%); AD=adenosine (% by weight to the weight of the SAMe ion); MTAD=methylthioadenosine (% by weight to the weight of the SAMe ion); SAMe=SAMe ion (mg/tablet-tbl); $V.B_6$=vitamin $B_6$ (mg/tbl); $V.B_{12}$=vitamin $B_{12}$ (mg/tbl); AF=folic acid (mg/tbl); SG=glucosamine sulfate (mg/tbl); MSM=methylsolfonylmethane (mg/tbl); SC=chondroitin sulfate (mg/tbl); the product SSB® 63 produced by G.T.C. is a mixture 1:1 of the sodium and ammonium salts of Shellac®

400 mg Tablets of SAMe/tbl

The following table illustrates the composition (amounts in mg/tbl) obtained by the process of the invention.

TABLE 1

| A. SAMe sulfate p-toluensulfonate | 830.0 |
| B. Calcium sulfate dihydrate | 166.00 |
| C. Calcium carbonate | 24.00 |
| D. Silica (Aerosil ®) | 10.00 |
| E. Glycerol Behenate (Compritol-e-ato ®) | 60.00 |
| F. Anhydrous Microcrystalline cellulose | 60.00 |
| Core Total weight | 1150.00 |
| G. Biogapress ® vegetal (Gattefossè) | 7.00 |
| H. Labrafac ® cc (Gattefossè) | 7.00 |
| I. Shellac ® (SSB ® 63 produced by G.T.C.) | 30.00 |
| L. Titanium dioxide | 15.00 |
| M. Talc | 15.00 |
| N. Triethylcitrate | 5.00 |
| O. Iron oxide ($Fe_2O_3$) | 0.10 |
| Tablet Total weight | 1229.10 |

Core Production:

1.1. Blending

The environment is conditioned at a temperature of 20° C. and at a relative humidity (R.H.) equal to about 20%. Compounds A–F, in the amounts shown in table 1, are put into a 200 l Viani biconical mixer and left under stirring, blending for about 30 minutes. At the end of this process step, the resulting mixture is transferred into dried recipients, maintaining humidity and temperature under control.

1.2. Pre-Compression

The pre-compression of the mixture is effected by a Ronchi AM rotative machine equipped with 18 round 25.0 mm punches. The hardness of the produced tablets has to be regulated so that a granulate can be then produced showing the following rheological characteristics:

dust rate equal to about 10% by weight, calculated by granulometry, considering as dust the fraction having particles showing an average dimension lower or equal to 50 μm.

1.3 Granulation

The tablets produced during the first processing step are granulated on a 1200 μm net always in a controlled humidity environment.

1.4 Compression

The final compression of the granulate is made by a Ronchi AM rotative machine equipped with 18 oblong 19.0×8.8 mm punches setting the weight at 1150 mg/tbl and the compression strength at about 245 N (equal to about 25 kiloponds: kp). The tablets obtained show a hardness equal to about 226–265 N (about 23–27 kp).

Friability: ≦1.0%; disaggregation time: ≦15 minutes (both measures have been effected according to the method described in the U.S. Pharmacopeia, U.S.P. XXIV ed.); K.F.≦2.0%; average weight variation: 1092.5–1207.5 mg.

Standard processing yield (ratio between the weight of the cores produced in step 1.4 and the total starting weight of the ingredients A–F): 97%.

The following table shows the stability tests carried out, on a single batch at 40° C. and at 75% R.H. for a period of six months, on the cores obtained after step 1.4; the table shows the impurities due to SAMe degradation, basically adenosine and methylthioadenosine, expressed as percentage to the weight of SAMe sulfate p-toluensulfonate per tablet. The samples have been preserved into closed and sealed glass bottles, to simulate the final packaging in aluminium/aluminium blisters.

TABLE 2

| Batch no 023 stability, 400 mg SAMe/tbl cores | | | | |
|---|---|---|---|---|
| Batch (T/t)[1] | K.F. | AD | MTAD | SAMe |
| 023 (20/0) | 1.87 | 0.43 | 1.06 | 419.01 |
| 023A (40/1) | 1.98 | 1.11 | 2.22 | 414.23 |
| 023B (40/3) | 1.84 | 1.99 | 3.04 | 402.02 |
| 023C (40/6) | 1.81 | 2.04 | 3.41 | 390.89 |

The data shown in Table 2 highlight the core stability, showing the total inertia of the excipients to SAMe.

2: Core Protection

The tablets obtained in the previous processing steps have been coated in a coater adding a mixture of Biogapress® vegetal (7.0 mg/tbl) and Labrafac® cc (7.0 mg/tbl).

In a 2.0 l glass container, Biogapress® vegetal and Labrafac® cc. were poured. The mixture was brought to a temperature of about 65° C. by thermostating, obtaining a homogeneous melted mass. After having pre-treated the coater at 65° C., about 115 kg of tablets were added, heating to 60° C. The melted mass previously prepared was poured on the tablets under stirring to protect the cores. The so treated cores were kept at 60° C. for about 15 minutes, till complete drying up of the coater basket from the oily layer. Then the in and out air flow was stopped and, leaving the coater open, the tablets were cooled at 37° C. When the polishing of the cores was good enough (after 10 minutes at 37° C.), about 200 g of talc were poured in the coater, letting the basket rotate for 5 minutes more and, bringing back the cores to 42–44° C., the gastroresistant coating was carried out.

3: Core Coating by Gastroresistant Film

In a container with proper dimension, Shellac® was solubilized at 50° C. till a 20% w/v solution was obtained and, under constant stirring, mixed slowly with triethylcitrate.

In another steel container equipped with stirrer, talc, titanium dioxide and iron oxide were dispersed in 4.0 l of deionized water. The resulting suspension was poured into the Shellac® solution washing the container with about 1.0 l of deionized water, then diluting with further 4.0 l of deionized water.

During the first step of the coating, the cores were maintained at a temperature of 44° C. for about 40 minutes, regularly lowering then the temperature, at regular intervals of time, till 42° C. were reached in the final step.

After ending the coating of the protected cores, they were let drying for further 10 minutes at 42° C. Finally, after waiting the lowering of temperature to 36–37° C., the coater was emptied, preserving the tablets in suitable humidity-proof envelopes.

Process yield (ratio between the number of tablets put into the coater and the number of filmed tablets): 99.8% (standard yield).

EXAMPLE 2

400 mg SAMe/tbl Tablets

The process described in Example 1 was repeated on an industrial scale using the components and the amounts (in kg) shown in the following table.

TABLE 3

| | | |
|---|---|---|
| A. SAMe sulfate p-toluensulfonate | 85.50 |
| B. Calcium Sulfate Dihydrate | 17.10 |
| C. Calcium Carbonate | 2.47 |
| D. Silica (Aerosil ®) | 1.03 |
| E. Glycerol Behenate (Compritol-e-ato ®) | 6.18 |
| F. Anhydrous Microcrystalline Cellulose | 6.18 |
| G. Biogapress ® vegetal (Gattefossè) | 0.70 |
| H. Labrafac ® cc (Gattefossè) | 0.70 |
| I. Shellac ® (SSB ® 63 of the G.T.C.) | 3.00 |
| L. Titanium dioxide | 1.50 |
| M. Talc | 1.50 |
| N. Triethylcitrate | 7.50 |
| O. Iron oxide ($Fe_2O_3$) | 0.01 |

The amounts refer to the preparation of a batch of 118.45 kg (103,000 tablets) for the components (A–F) regarding the preparation of the core, while for the coating (G–O), the amounts refer to the preparation of a batch of 115.00 kg (100,000 tablets).

EXAMPLE 3

200 mg SAMe/tbl Tablets

Tablets having the composition (amounts in mg/tbl) shown in following table have been manufactured according to the process described in Example 1.

TABLE 4

| | |
|---|---|
| A. SAMe sulfate p-toluensulfonate | 415.0 |
| B. Calcium Sulfate Dihydrate | 83.0 |
| C. Calcium Carbonate | 12.0 |
| D. Silica (Aerosol) | 5.0 |
| E. Glycerol Behenate (Compritol-e-ato ®) | 30.0 |
| F. Anhydrous Microcrystalline Cellulose | 30.0 |
| Total core weight | 575.0 |

TABLE 4-continued

| | |
|---|---|
| G. Biogapress ® vegetal (Gaftefossè) | 3.5 |
| H. Labrafac ® cc (Gattefossè) | 3.5 |
| I. Shellac ® (SSB ® 63 of the G.T.C.) | 15.0 |
| L. Titanium dioxide | 7.5 |
| M. Talc | 7.5 |
| N. Triethylcitrate | 2.5 |
| O. Iron oxide ($Fe_2O_3$) | 0.1 |
| Tablet Total weight | 614.6 |

However, in step 1.4, the granulate was compressed by a Ronchi AM rotative machine, equipped with 18 round 11.0 mm punches, adjusting the weight to 575 mg/tbl and the compression strength to about 25 kp. The tablets obtained showed a hardness between 23 and 27 kp.

Average weight variation: 546.25–603.75 mg.

TABLE 5

Batch no. 015 stability, 200 mg SAMe/tbl cores

| Batch (T/t) | K.F. | AD | MTAD | SAMe |
|---|---|---|---|---|
| 015 (20/0) | 1.77 | 0.45 | 1.86 | 238.11 |
| 015A (40/1) | 1.88 | 1.51 | 4.82 | 235.56 |
| 015B (40/3) | 1.99 | 1.85 | 5.45 | 225.23 |
| 015C (40/6) | 2.05 | 2.34 | 5.83 | 228.13 |

The data of Table 5 show the excellent stability of the cores, and confirm the inertia of the selected excipients to SAMe.

As a proof of the efficacy of the protective coating of the cores according the process of the invention, the following table shows the results concerning the weight increase of two batches of 200 mg SAMe/tbl cores, prepared as described in the following example (017—protected by Biogapress® vegetal and Labrafac® cc; batch 018—not protected) left for 7 days at 20° C. and to 20% R.H or exposed for the same period of time at 40° C. and to 75%. R.H.

TABLE 6

| Batch | T/R.H. | K.F. |
|---|---|---|
| 017 | 20/20 | 2.10 |
| 017 | 40/50 | 3.31 |
| 018 (comparison) | 20/20 | 1.79 |
| 018 (comparison) | 40/50 | 6.51 |

EXAMPLE 4

200 mg SAMe/tbl Tablets

The process described in Example 2 was repeated on an industrial scale using the components and amounts (in kg) shown in the following table.

TABLE 7

| | |
|---|---|
| A. SAMe sulfate p-toluensulfonate | 85.50 |
| B. Calcium Sulfate Dihydrate | 17.10 |
| C. Calcium Carbonate | 2.47 |
| D. Silica (Aerosil ®) | 1.03 |
| E. Glycerol Behenate (Compritol-e-ato ®) | 6.18 |
| F. Anhydrous Microcrystalline Cellulose | 6.18 |
| G. Biogapresse ® vegetal (Gattefossè) | 0.70 |
| H. Labrafac ® cc (Gattefossè) | 0.70 |
| I. Shellac ® (SSB ® 63 of the G.T.C.) | 3.00 |

TABLE 7-continued

| | | |
|---|---|---|
| L. | Titanium dioxide | 1.50 |
| M. | Talc | 1.50 |
| N. | Triethylcitrate | 0.50 |
| O. | Iron oxide ($Fe_2O_3$) | 0.010 |

The amounts refer to the preparation of a batch of 118.45 kg (206,000 tablets) for the components (A–F) concerning the preparation of the core whereas, as to the coating (G–O), the amounts refer to the preparation of a batch of 115.00 kg (200,000 tablets).

EXAMPLE 5

Tablets Comprising 600 mg of SAMe/tbl+Vitamins $B_6/B_{12}$ and Folic Acid.

Tablets having the composition (amounts in mg/tbl) shown in the following table have been manufactured according to the process described in Example 1

TABLE 8

| | | |
|---|---|---|
| A. | SAMe sulfate p-toluensulfonate | 1245.0 |
| B. | Vitamin $B_6$ | 3.0 |
| C. | Vitamin $B_{12}$ | 1.0 |
| D. | Folic acid | 0.8 |
| E. | Calcium sulfate dihydrate | 249.0 |
| F. | Calcium carbonate | 36.0 |
| G. | Silica (Aerosil ®) | 15.0 |
| H. | Glycerol Behenate (Compritol-e-ato ®) | 90.0 |
| I. | Anhydrous Microcrystalline cellulose | 90.0 |
| | Core total weight | 1729.8 |
| G. | Biogapress ® vegetal (Gattefossè) | 10.5 |
| H. | Labrafac ® cc (Gattefossè) | 10.5 |
| I. | Shellac ® (SSB ® 63 produced by G.T.C.) | 43.5 |
| L. | Titanium dioxide | 22.5 |
| M. | Talc | 22.5 |
| N. | Triethylcitrate | 7.5 |
| O. | Ferric oxide ($Fe_2O_3$) | 0.1 |
| | Tablet Total weight | 1846.9 |

However, in step 1.4, the granulate was obtained by a Ronchi AM rotative machine, equipped with 18 oblong 23.6×10.8 mm punches, adjusting the weight to 1729.80 mg/tbl and the compression strength to about 25 kp. The tablets produced had a hardness between 23 and 27 kp.

Average weight variation: 1643.31–1816.29 mg.

TABLE 9

Batch no 026 stability, 600 mg SAMe/tbl cores

| Batch (T/t) | K.F. | AD | MTAD | SAMe | V. $B_6$ | V. $B_{12}$ | AF |
|---|---|---|---|---|---|---|---|
| 026 (20/0) | 1.89 | 0.54 | 1.12 | 632.11 | 3.06 | 1.05 | 0.84 |
| 026A (40/1) | 1.75 | 1.41 | 3.45 | 612.23 | 2.94 | 1.02 | 0.85 |
| 026B (40/3) | 1.97 | 1.77 | 4.12 | 606.89 | 2.86 | 1.03 | 0.82 |
| 026C (40/6) | 2.07 | 2.45 | 5.36 | 580.56 | 2.77 | 0.99 | 0.80 |

The data of Table 9 show the excellent stability of the cores, and confirm the total inertia of the selected excipients to SAMe and to the other active ingredients.

EXAMPLE 6

Tablets Comprising 600 mg of SAMe/tbl+Vitamins $B_6/B_{12}$ and Folic Acid.

The process described in Example 5 was repeated on an industrial scale using the components and amounts (in kg) shown in the following table.

TABLE 10

| | | |
|---|---|---|
| A. | SAMe sulfate p-toluensulfonate | 85.500 |
| B. | Vitamin $B_6$ | 0.210 |
| C. | Vitamin $B_{12}$ | 0.069 |
| D. | Folic acid | 0.055 |
| E. | Calcium sulfate dihydrate | 17.100 |
| F. | Calcium carbonate | 2.470 |
| G. | Silica (Aerosil ®) | 1.030 |
| H. | Glycerol Behenate (Compritol-e-ato ®) | 6.180 |
| I. | Anhydrous Microcrystalline cellulose | 6.180 |
| L. | Biogapress ® vegetal (Gattefossè) | 0.700 |
| M. | Labrafac ® cc (Gattefossè) | 0.700 |
| N. | Shellac ® (SSB ® 63 produced by G.T.C.) | 2.900 |
| O. | Titanium dioxide | 1.500 |
| P. | Talc | 1.500 |
| Q. | Triethylcitrate | 0.500 |
| R. | Iron oxide ($Fe_2O_3$) | 0.010 |

The amounts refer to the preparation of a batch of 118.78 kg (68,666 tablets) for the components (A–I) concerning the preparation of the cores, whereas, as to coating (L–R), the amounts refer to the preparation of a batch of 115.33 kg (66,672 tablets).

EXAMPLE 7

Tablets Comprising 400 mg of SAMe/tbl+Vitamins $B_6/B_{12}$ and Folic Acid.

Tablets having the composition (amounts in mg/tbl) shown in the following table have been manufactured according to the process described in Example 1.

TABLE 11

| | | |
|---|---|---|
| A. | SAMe sulfate p-toluensulfonate | 830.0 |
| B. | Vitamin $B_6$ | 3.0 |
| C. | Vitamin $B_{12}$ | 1.0 |
| D. | Folic acid | 0.8 |
| E. | Calcium sulfate dihydrate | 166.0 |
| F. | Calcium carbonate | 24.0 |
| G. | Silica (Aerosil ®) | 10.0 |
| H. | Glycerol Behenate (Compritol-e-ato ®) | 60.0 |
| I. | Anhydrous Microcrystalline cellulose | 60.0 |
| | Core Total weight | 1154.8 |
| G. | Biogapress ® vegetal (Gattefossè) | 7.0 |
| H. | Labrafac ® cc (Gattefossè) | 7.0 |
| I. | Shellac ® (SSB ® 63 produced by G.T.C.) | 30.0 |
| L. | Titanium dioxide | 15.0 |
| M. | Talc | 15.0 |
| N. | Triethylcitrate | 5.0 |
| O. | Ferric oxide ($Fe_2O_3$) | 0.1 |
| | Tablet Total weight | 1233.9 |

However, in step 1.4, the granulate was obtained by a Ronchi AM rotative machine equipped with 18 oblong 19.0×8.8 mm punches, adjusting the weight to 1154.80 mg/tbl and the compression strength to about 25 kp. The tablets produced had a hardness between 23 and 27 kp.

Average weight variation: 1097.06–1212.54 mg.

TABLE 12

Batch no. 029 stability, 400 mg SAMe/tbl cores.

| Batch (T/t) | (K.F.) | AD | MTAD | SAMe | V. $B_6$ | V. $B_{12}$ | AF |
|---|---|---|---|---|---|---|---|
| 029 (20/0) | 1.75 | 0.41 | 1.25 | 412.11 | 3.07 | 1.03 | 0.82 |
| 029A (40/1) | 1.79 | 1.12 | 2.88 | 407.65 | 3.02 | 1.00 | 0.87 |

TABLE 12-continued

Batch no. 029 stability, 400 mg SAMe/tbl cores.

| Batch (T/t) | (K.F.) | AD | MTAD | SAMe | V. B$_6$ | V. B$_{12}$ | AF |
|---|---|---|---|---|---|---|---|
| 029B (40/3) | 1.87 | 1.37 | 3.45 | 398.73 | 2.98 | 1.02 | 0.85 |
| 029C (40/6) | 1.96 | 2.04 | 4.78 | 380.58 | 2.87 | 1.01 | 0.81 |

The data of Table 12 highlight the excellent stability of the cores, and confirm the total inertia of the selected excipients to SAMe and to the other active ingredients.

EXAMPLE 8

Tablets Comprising 400 mg Tablets of SAMe/tbl+Vitamins B$_6$/B$_{12}$ and Folic Acid.

The process described in Example 7 was repeated on an industrial scale using components and amounts (in kg) shown in the following table.

TABLE 13

| A. SAMe sulfate p-toluensulfonate | 85.500 |
|---|---|
| B. Vitamin B$_6$ | 0.210 |
| C. Vitamin B$_{12}$ | 0.069 |
| D. Folic acid | 0.055 |
| E. Calcium sulfate dihydrate | 17.100 |
| F. Calcium carbonate | 2.470 |
| G. Silica (Aerosil ®) | 1.030 |
| H. Glycerol Behenate (Compritol-e-ato ®) | 6.180 |
| I. Anhydrous Microcrystalline cellulose | 6.180 |
| G. Biogapress ® vegetal (Gattefossè) | 0.700 |
| H. Labrafac ® cc (Gattefossè) | 0.700 |
| I. Shellac ® (SSB ® 63 produced by G.T.C.) | 3.000 |
| L. Titanium dioxide | 1.500 |
| M. Talc | 1.500 |
| N. Triethylcitrate | 0.500 |
| O. Ferric oxide (Fe$_2$O$_3$) | 0.010 |

The amounts refer to the preparation of a batch of 118.78 kg (103,000 tablets) for the compounds (A–I) concerning the preparation of the cores, whereas, as to the coating (L–R), the amounts refer to the preparation of a batch of 115.33 kg (100,000 tablets).

EXAMPLE 9

Tablets Comprising 200 mg Tablets of SAMe/tbl+500 mg of Glucosamine Sulfate/tbl.

The following table illustrates the composition (amounts in mg/tbl) per each tablet obtained by the process of the invention.

TABLE 14

| A. SAMe sulfate p-toluensulfonate | 415.0 |
|---|---|
| B. Glucosamine sulfate | 500.0 |
| C. Calcium sulfate dihydrate | 30.0 |
| D. Calcium carbonate | 12.0 |
| E. Silica FK 160 | 10.0 |
| F. Glycerol Behenate (Compritol-e-ato ®) | 60.0 |
| G. Anhydrous Microcrystalline cellulose | 253.0 |
| Core total weight | 1280.0 |
| H. Biogapress ® vegetal (Gattefossè) | 7.0 |
| I. Labrafac ® cc (Gattefossè) | 7.0 |
| L. Shellac ® (SSB ® 63 produced by G.T.C.) | 32.0 |
| M. Titanium dioxide | 15.0 |
| N. Talc | 15.0 |
| O. Triethylcitrate | 5.0 |
| P. Ferric oxide (Fe$_2$O$_3$) | 0.1 |
| Tablet total weight | 1361.1 |

Core Production:

1.1 Blending

The environment was conditioned at a temperature of 20° C. and at a relative humidity R.H. of about 20%. In pair (A–B) (C–D) (50 mg of F and 200 mg of G) and finally E, the components were put, in the amounts and in the order indicated in table 14, into a 200 l Viani biconical mixer, blending each group of compounds for about 10 minutes. Silica was finally added and blended for further 10 minutes then transferring for further 10 minutes the resulting mixture into dry containers, while controlling both humidity and temperature.

1.2 Precompression: According to What Described in Example 1

1.3. Granulation and Blending

The tablets resulting from the previous step were granulated on a 1200 μm net, while checking the humidity. Then, the resulting granulate was blended again, into a 200 l Viani mixer, with the remaining amounts of microcrystalline cellulose and Compritol-e-ato® (53 and 10 mg respectively).

1.4 Compression

The final compression of the granulate was carried out by a Ronchi AM rotative machine, equipped with 18 oblong 19.0×8.8 mm punches, adjusting the weight to 1280.8 mg/tbl and the compression strength to about 25 kp. The produced tablets showed a hardness between 23 and 27 kp.

Average weight variation: 1216.0–1344.0 mg

Friability, humidity and standard yield were found to conform to what illustrated in Example 1.

TABLE 15

Batch no. 032 stability, 200 mg SAMe/tbl cores

| Batch (T/t) | (K.F.) | AD | MTAD | SAMe | S.G. |
|---|---|---|---|---|---|
| 032 (20/0) | 1.38 | 0.34 | 1.52 | 217.98 | 502.06 |
| 032A (40/1) | 1.26 | 1.01 | 3.78 | 215.42 | 501.94 |
| 032B (40/3) | 1.15 | 1.23 | 4.89 | 205.52 | 500.12 |
| 032C (40/6) | 1.32 | 2.02 | 5.98 | 200.47 | 501.45 |

The data in Table 15 highlight the excellent stability of the cores, and confirm the total inertia of the selected excipients to SAMe and to glucosamine sulfate.

The protection of the cores and the gastroresistant filming were carried out according to that described in Example 1.

EXAMPLE 10

Tablets Comprising 200 mg of SAMe/tbl+500 mg of Glucosamine Sulfate/tbl.

The process described in Example 9 was repeated on an industrial scale using components and amounts (in kg) shown in the following table.

TABLE 16

| A. SAMe sulfate p-toluensulfonate | 42.74 |
|---|---|
| B. Glucosamine sulfate | 51.50 |
| C. Calcium Sulfate Dihydrate | 3.09 |
| D. Calcium Carbonate | 1.23 |
| E. Silica FK 160 | 1.03 |
| F. Glycerol Behenate (Compritol-e-ato ®) | 6.18 |
| G. Anhydrous Microcrystalline Cellulose | 26.06 |
| H. Biogapress ® vegetal (Gattefossè) | 0.70 |
| I. Labrafac ® cc (Gattefossè) | 0.70 |
| L. Shellac ® (SSB ® 63 produced by G.T.C.) | 3.20 |
| M. Titanium dioxide | 1.50 |
| N. Talc | 1.50 |
| O. Triethylcitrate | 0.50 |
| P. Iron oxide (Fe$_2$O$_3$) | 0.01 |

The amounts refer to the preparation of a batch of 131.8 kg (103,000 tablets) for the components (A–G) concerning the preparation of the cores, whereas as to the coating (H–P), the amounts refer to the preparation of a batch of 128.0 kg (100,000 tablets).

EXAMPLE 11

Tablets Comprising 200 mg of SAMe/tbl+500 mg of Methylsulfonylmethane (MSM)/tbl

Tablets having the composition (amounts in g/tbl) shown in the following table according to the details described in Example 1.

TABLE 17

| | |
|---|---|
| A. SAMe sulfate p-toluensulfonate | 415.0 |
| B. MSM | 500.0 |
| C. Calcium sulfate dihydrate | 30.0 |
| D. Calcium carbonate | 12.0 |
| E. Silica FK 160 | 10.0 |
| F. Glycerol Behenate (Compritol-e-ato ®) | 60.0 |
| G. Anhydrous Microcystalline cellulose | 253.0 |
| Core total weight | 1280.0 |
| H. Biogapress ® vegetal (Gattefossè) | 7.0 |
| I. Labrafac ® cc (Gattefossè) | 7.0 |
| L. Shellac ® (SSB ® 63 produced by G.T.C.) | 32.0 |
| M. Titanium dioxide | 15.0 |
| N. Talc | 15.0 |
| O. Triethylcitrate | 5.0 |
| P. Ferric oxide (Fe$_2$O$_3$) | 0.1 |
| Tablet Total weight | 1361.1 |

However, the blending and granulation steps were carried out according to what described in Example 9, whereas the compression of the granulate was carried out by a Ronchi AM rotative machine equipped with 18 oblong 19.0×8.8 mm punches, adjusting the weight to 1280.0 mg/tbl and the compression strength to about 25 kp. The produced tablets showed a hardness between 23 and 27 kp.

Average weight variation: 1216.0–1344.0 mg.

TABLE 18

Batch no. 035 stability, 200 mg SAMe/tbl cores

| Batch (T/t) | K.F | AD | MTAD | SAMe | MSM |
|---|---|---|---|---|---|
| 035 (20/0) | 1.42 | 0.40 | 1.36 | 210.23 | 500.12 |
| 035A (40/1) | 1.35 | 1.45 | 2.99 | 203.58 | 501.45 |
| 035B (40/3) | 1.74 | 1.73 | 3.75 | 201.86 | 496.56 |
| 035C (40/6) | 1.15 | 2.52 | 4.12 | 194.63 | 498.01 |

The data in Table 18 show the excellent stability of the cores, and confirm the total inertia of the selected excipients as to SAMe and to glucosamine sulfate.

EXAMPLE 12

Tablets Comprising 200 mg of SAMe/tbl+500 mg of Methylsulfonylmethane (MSM)/tbl

The process described in Example 11 was repeated on an industrial scale using the components and amounts (in kg) shown in the following table.

TABLE 19

| | |
|---|---|
| A. SAMe sulfate p-toluensulfonate | 42.74 |
| B. Metilsulfonilmethane MSM | 51.50 |
| C. Calcium sulfate dihydrate | 3.09 |
| D. Calcium carbonate | 1.23 |
| E. Silica FK 160 | 1.03 |
| F. Glycerol Behenate (Compritol-e-ato ®) | 6.18 |
| G. Anhydrous Microcrystalline cellulose | 26.06 |
| H. Biogapress ® vegetal (Gattefossè) | 0.70 |
| I. Labrafac ® cc (Gattefossè) | 0.70 |
| L. Shellac ® (SSB ® 63 produced by G.T.C.) | 3.20 |
| M. Titanium dioxide | 1.50 |
| N. Talc | 1.50 |
| O. Triethylcitrate | 0.50 |
| P. Ferric oxide (Fe$_2$O$_3$) | 0.01 |

The amounts refer to the preparation of a batch of 131.8 kg (103,000 tablets) for the components (A–G) concerning the preparation of the cores whereas, the amounts regarding the coating (H–P) refer to the preparation of a batch of 128.0 kg (100,000 tablets).

EXAMPLE 13

Tablets Comprising 200 mg of SAMe ion/tbl+400 mg of Chondroitin Sulfate

Tablets having the composition (amounts in g/tbl) shown in the following table were produced according to what described in Example 1.

TABLE 20

| | |
|---|---|
| A. SAMe sulfate p-toluensulfonate | 415.0 |
| B. Chondroitin sulfate | 400.0 |
| C. Calcium sulfate dihydrate | 123.0 |
| D. Calcium carbonate | 12.0 |
| E. Silica FK 160 | 10.0 |
| F. Glycerol Behenate (Compritol-e-ato ®) | 60.0 |
| G. Anhydrous Microcystalline cellulose | 130.0 |
| Core total weight | 1150.0 |
| H. Biogapress ® vegetal (Gattefossè) | 7.0 |
| I. Labrafac ® cc (Gattefossè) | 7.0 |
| L. Shellac ® (SSB ® 63 produced by G.T.C.) | 30.0 |
| M. Titanium dioxide | 15.0 |
| N. Talc | 15.0 |
| O. Triethylcitrate | 5.0 |
| P. Ferric oxide (Fe$_2$O$_3$) | 0.1 |
| Tablet Total weight | 1229.1 |

However, in step 1.4, the granulate was compressed by a Ronchi AM rotative machine equipped with 18 oblong 19.0×8.8 mm punches, adjusting the weight to 1150 mg/tbl and the compression strength to about 25 kp. The produced tablets showed a hardness between 23 and 27 kp.

Average weight variation: 1092.5–1207.5 mg

TABLE 21

Batch no. 038 stability, 200 mg SAMe/tbl cores

| Batch (T/t) | K.F. | AD | MTAD | SAMe | SC |
|---|---|---|---|---|---|
| 038 (20/0) | 2.12 | 0.33 | 1.26 | 214.89 | 398.85 |
| 038A (40/1) | 2.24 | 1.55 | 2.25 | 208.36 | 396.44 |
| 038B (40/3) | 2.09 | 1.78 | 3.36 | 202.12 | 397.36 |
| 038C (40/6) | 1.97 | 2.69 | 4.42 | 198.78 | 393.45 |

The data in Table 21 show the excellent stability of the cores, and confirm the total inertia of the selected excipients as to SAMe and to chondroitin sulfate.

EXAMPLE 14

Tablets Comprising 200 mg of SAMe/tbl+400 mg of Chondroitin Sulfate/tbl

The process described in Example 13 was repeated on an industrial scale using the components and amounts (in kg) shown in the following table.

TABLE 22

| | |
|---|---|
| A. SAMe solfate p-toluensulfonate | 42.74 |
| B. Chondroitin sulfate | 41.20 |
| C. Calcium sulfate dihydrate | 12.67 |
| D. Calcium carbonate | 1.23 |
| E. Silica FK 160 | 1.03 |
| F. Glycerol Behenate (Compritol-e-ato ®) | 6.18 |
| G. Anhydrous Microcrystalline cellulose | 13.39 |
| H. Biogapress ® vegetal (Gattefossè) | 0.70 |
| I. Labrafac ® cc (Gattefossè) | 0.70 |
| L. Shellac ® (SSB ® 63 produced by G.T.C.) | 3.00 |
| M. Titanium dioxide | 1.50 |
| N. Talc | 1.50 |
| O. Triethylcitrate | 0.50 |
| P. Ferric oxide ($Fe_2O_3$) | 0.01 |

The amounts refer to the preparation of a batch of 118.45 kg (103,000 tablets) for the components (A–G) concerning the preparation of the core, whereas, the amounts regarding the coating (H–P) refer to the preparation of a batch of 115.00 kg (100,000 tablets).

EXAMPLE 15

Tablets comprising 200 mg of SAMe/tbl+400 mg of chondroitin sulfate/tbl+500 mg glucosamine sulfate/tbl.

The following table shows the composition (amounts in mg/tbl) per each tablet obtained by the process of the invention.

TABLE 23

| | |
|---|---|
| A. SAMe sulfate p-toluensulfonate | 415.0 |
| B. Chondroitin sulfate | 400.0 |
| C. Glucosamine sulfate | 500.0 |
| D. Calcium sulfate dihydrate | 20.0 |
| E. Calcium carbonate | 12.0 |
| F. Silica FK 160 | 15.0 |
| G. Glycerol Behenate (Compritol-e-ato ®) | 70.0 |
| H. Anhydrous Microcrystalline cellulose | 268.0 |
| Core total weight | 1700.0 |
| I. Biogapress ® vegetal (Gattefossè) | 10.0 |
| L. Labrafac ® cc (Gattefossè) | 10.0 |
| M. Shellac ® (SSB ® 63 produced by G.T.C.) | 42.5 |
| N. Titanium dioxide | 21.0 |
| O. Talc | 21.0 |
| P. Triethylcitrate | 7.5 |
| Q. Ferric oxide ($Fe_2O_3$) | 0.1 |
| Tablet Total weight | 1811.6 |

Core Production:

1.1. Blending

The environment was conditioned at a temperature of 20° C. and at a relative humidity of about 20% R.H. The (A,B,C), (D,E) and (60 mg of G and 200 mg of H) and finally E components, in the amounts and in the order indicated in table 23, were put into a 200 l Viani biconical mixer, blending each group of substances for about 10 minutes. Finally the silica was added and blended for further 10 minutes putting the resulting mixture into dry containers, always checking both humidity and temperature.

1.2. Precompression: According to What Described in Example 1

1.3 Granulation and Blending

The tablets obtained during the first process step were granulated on a 1200 μm net in a controlled humidity environment. Then, in the 200 l Viani mixer, the obtained granulate was blended again with the remaining amounts of microcrystalline cellulose and compritol-e-ato® (68 and 10 mg, respectively)

1.4 Compression

The final compression of the granulate was carried out by a Ronchi AM rotative machine equipped with 18 mm oblong 23.6×10.8 mm punches, adjusting the weight to 1700 mg/tbl and the compression strength to about 25 kp. The produced tablets showed a hardness between 23 and 27 kp.

Average weight variation: 1615.0–1785.0 mg

Friability, humidity and standard yield resulted to be in accordance with Example 1.

TABLE 24

Batch no. 041 stability, 200 mg SAMe/tbl cores

| Batch (T/t) | K.F. | AD | MTAD | SAMe | MSM | SC |
|---|---|---|---|---|---|---|
| 041 (20/0) | 1.97 | 0.25 | 1.11 | 232.78 | 506.06 | 400.05 |
| 041A (40/1) | 1.75 | 0.85 | 3.00 | 226.23 | 500.94 | 402.14 |
| 041B (40/3) | 1.56 | 1.12 | 3.89 | 219.56 | 496.78 | 398.85 |
| 041C (40/6) | 2.00 | 2.00 | 4.89 | 214.59 | 499.77 | 397.56 |

The data in Table 24 show the excellent stability of the cores, and confirm the total inertia of the selected excipients as to SAMe and to the other active ingredients.

EXAMPLE 16

Tablets Comprising 200 mg of SAMe/tbl+400 mg of Chondroitin Sulfate/tbl+500 mg of Glucosamine Sulfate/cpr.

The process described in Example 15 was repeated on an industrial scale using the components and amounts (in kg) shown in the following table.

TABLE 25

| | |
|---|---|
| A. SAMe sulfate p-toluensulfonate | 29.900 |
| B. Chondroitin sulfate | 28.820 |
| C. Glucosamine sulfate | 36.030 |
| D. Calcium sulfate dihydrate | 1.440 |
| E. Calcium carbonate | 0.860 |
| F. Silica FK 160 | 1.080 |
| G. Glycerol Behenate (Compritol-e-ato ®) | 5.040 |
| H. Anhydrous Microcrystalline cellulose | 19.300 |
| I. Biogapress ® vegetal (Gattefossè) | 0.700 |
| L. Labrafac ® cc (Gattefossè) | 0.700 |
| M. Shellac ® (SSB ® 63 produced by G.T.C.) | 2.970 |
| N. Titanium dioxide | 1.470 |
| O. Talc | 1.470 |
| P. Triethylcitrate | 0.520 |
| Q. Ferric oxide ($Fe_2O_3$) | 0.007 |

The amounts refer to the preparation of a batch of 122.57 kg (72,100 tablets) for the components (A–H) concerning the preparation of the core whereas, as to the coating (I–Q), the amounts refer to the preparation of a batch of 119.00 kg (70,000 tablets).

Stability Trials on the Finished Product

The stability of the compositions obtainable by the process of the invention and referring to the above mentioned odd examples both at 40° C. and 75% R.H. (STRESS TEST) and at long-term room temperature (SHELF LIFE), were evaluated on the basis of their aspect change (mainly, colour change), titre (mg/tbl) of the SAMe ion and of the other active ingredients, humidity increase (K.F.) and impurities due to SAMe degradation; the presence of possible degradation products, substantially adenosine and mehtylthioadenosine, expressed as percentages to the weight of SAMe sulfate p-toluensulfonate per tablet, was further controlled by HPLC.

Stress Test

The tablets have been packed in closed and sealed glass bottles so as to simulate the final packaging (usually, aluminium/aluminium blister).

The samples thus prepared, were kept in a oven (Kottermann) for a period of six months, thermostated at 40±2° C. 75% R.H.

Nine samples from three different batches were used for the 200 mg tablets (Es. 3, 9, 11, 13, 15) and further nine samples from three different batches were used for the 400 and 600 mg tablets (Ex. 1, 5, 7) wherein for each sample, any batch was sampled after 0,1, 3, and 6 months.

TABLE 26

Batch no. 023- 400 mg SAMe/tbl tablets (EX. 1)

| Batch (T/t) | K.F. | AD | MTAD | SAMe |
|---|---|---|---|---|
| 023 (20/0) | 1.78 | 0.31 | 1.16 | 422.42 |
| 023A (40/1) | 1.86 | 1.14 | 1.45 | 411.19 |
| 023B (40/3) | 1.85 | 1.95 | 3.44 | 399.12 |
| 023C (40/6) | 1.89 | 2.24 | 3.89 | 384.67 |

TABLE 27

Batch no. 024- 400 mg SAMe/tbl tablets (EX. 1)

| Batch (T/t) | (K.F.) | AD | MTAD | SAMe |
|---|---|---|---|---|
| 024 (20/0) | 1.86 | 0.31 | 1.27 | 423.93 |
| 024A (40/1) | 1.91 | 1.05 | 1.89 | 409.78 |
| 024B (40/3) | 1.59 | 1.72 | 3.37 | 395.37 |
| 024C (40/6) | 1.81 | 1.84 | 4.53 | 385.67 |

TABLE 28

Batch no. 025- 400 mg SAMe/tbl tablets (EX. 1)

| Batch (T/t) | (K.F.) | AD | MTAD | SAMe |
|---|---|---|---|---|
| 025 (20/0) | 1.70 | 0.47 | 1.42 | 423.51 |
| 025A (40/1) | 1.76 | 1.04 | 2.35 | 415.19 |
| 025B (40/3) | 1.85 | 1.78 | 3.36 | 411.36 |
| 025C (40/6) | 1.73 | 2.82 | 3.20 | 381.58 |

TABLE 29

Batch no. 015 stability, 200 mg SAMe/tbl tablets (EX. 3)

| Batch (T/t) | (K.F.) | AD | MTAD | SAMe |
|---|---|---|---|---|
| 015 (20/0) | 1.89 | 0.42 | 2.08 | 240.60 |
| 015A (40/1) | 1.98 | 1.81 | 5.05 | 233.9 |
| 015B (40/3) | 2.23 | 1.78 | 6.05 | 218.62 |
| 015C (40/6) | 1.62 | 2.54 | 6.41 | 227.51 |

TABLE 30

Batch no. 017- 200 mg SAMe/tbl tablets (EX. 3)

| Batch (T/t) | (K.F.) | AD | MTAD | SAMe |
|---|---|---|---|---|
| 017 (20/0) | 2.11 | 0.34 | 1.56 | 216.22 |
| 017A (40/1) | 2.18 | 1.55 | 2.89 | 213.43 |
| 017B (40/3) | 2.08 | 1.63 | 5.45 | 199.16 |
| 017C (40/6) | 1.81 | 2.21 | 6.79 | 193.21 |

TABLE 31

Batch no. 018- 200 mg SAMe/tbl tablets (EX. 3)

| Batch (T/t) | (K.F.) | AD | MTAD | SAMe |
|---|---|---|---|---|
| 018 (20/0) | 1.65 | 0.29 | 1.83 | 211.20 |
| 018A (40/1) | 1.95 | 1.04 | 2.55 | 202.30 |
| 018B (40/3) | 1.77 | 1.88 | 3.36 | 196.25 |
| 018C (40/6) | 1.65 | 2.35 | 4.45 | 190.20 |

TABLE 32

Batch no. 026 stability, 600 mg SAMe/tbl tablets (EX. 5)

| Batch (T/t) | K.F. | AD | MTAD | SAMe | V.$B_6$ | V.$B_{12}$ | AF |
|---|---|---|---|---|---|---|---|
| 026 (20/0) | 2.22 | 0.39 | 1.22 | 630.56 | 3.07 | 1.03 | 0.83 |
| 26A (40/1) | 2.05 | 1.48 | 3.23 | 615.45 | 2.97 | 1.00 | 0.85 |
| 26B (40/3) | 2.18 | 1.97 | 4.52 | 601.25 | 2.89 | 1.02 | 0.80 |
| 26C (40/6) | 2.27 | 2.88 | 4.99 | 577.22 | 2.75 | 0.99 | 0.79 |

TABLE 33

Batch no. 027- 600 mg SAMe/tbl tablets (EX. 5)

| Batch (T/t) | K.F. | AD | MTAD | SAMe | V. $B_6$ | V. $B_{12}$ | AF |
|---|---|---|---|---|---|---|---|
| 027 (20/0) | 1.58 | 0.55 | 1.57 | 627.67 | 3.10 | 1.10 | 0.89 |
| 27A (40/1) | 1.57 | 1.31 | 3.15 | 602.99 | 3.05 | 1.04 | 0.84 |
| 27B (40/3) | 1.97 | 1.99 | 4.72 | 589.11 | 2.96 | 1.07 | 0.80 |
| 27C (40/6) | 2.17 | 2.77 | 5.86 | 571.98 | 2.87 | 1.01 | 0.85 |

TABLE 34

Batch 028- 600 mg SAMe/tbl tablets (EX. 5)

| Batch (T/t)[1] | K.F. | AD | MTAD | SAMe | V. $B_6$ | V. $B_{12}$ | Folic Ac. |
|---|---|---|---|---|---|---|---|
| 028 (20/0) | 2.05 | 0.44 | 1.28 | 635.88 | 3.03 | 1.02 | 0.80 |
| 028A (40/1) | 1.85 | 1.60 | 2.55 | 613.89 | 2.99 | 1.02 | 0.79 |
| 028B (40/3) | 1.97 | 1.79 | 3.99 | 602.12 | 2.89 | 1.00 | 0.80 |
| 028C (40/6) | 2.22 | 2.55 | 4.89 | 582.47 | 2.70 | 0.95 | 0.74 |

TABLE 35

Batch no. 029 stability, 400 mg SAMe/tbl tablets (EX. 7)

| Batch (T/t)[1] | K.F. | AD | MTAD | SAMe | V.$B_6$ | V.$B_{12}$ | Folic Ac. |
|---|---|---|---|---|---|---|---|
| 029 (20/0) | 1.95 | 0.31 | 1.42 | 415.91 | 3.01 | 1.02 | 0.82 |
| 029A (40/1) | 2.02 | 1.52 | 2.58 | 409.35 | 2.89 | 1.01 | 0.85 |
| 029B (40/3) | 1.98 | 1.77 | 3.12 | 400.45 | 2.98 | 1.07 | 0.80 |
| 029C (40/6) | 2.12 | 2.84 | 4.69 | 380.11 | 2.80 | 0.97 | 0.84 |

TABLE 36

Batch no. 030 - 400 mg SAMe tablets/tbl (EX. 7)

| Batch (T/t)[1] | K.F. | AD | MTAD | SAMe | V.B$_6$ | V.B$_{12}$ | Folic Ac. |
|---|---|---|---|---|---|---|---|
| 030 (20/0) | 2.05 | 0.55 | 1.59 | 421.01 | 3.11 | 1.01 | 0.79 |
| 030A (40/1) | 2.10 | 1.26 | 2.96 | 414.58 | 3.11 | 1.00 | 0.81 |
| 030B (40/3) | 1.99 | 1.75 | 3.78 | 401.69 | 3.05 | 1.02 | 0.78 |
| 030C (40/6) | 1.95 | 2.58 | 5.25 | 382.56 | 2.89 | 0.97 | 0.80 |

TABLE 37

Batch no. 031 - 400 mg SAMe/tbl tablets (EX. 7)

| Batch (T/t)[1] | K.F. | AD | MTAD | SAMe | V.B$_6$ | V.B$_{12}$ | Folic Ac. |
|---|---|---|---|---|---|---|---|
| 031 (20/0) | 1.87 | 0.47 | 1.72 | 417.56 | 3.12 | 1.04 | 0.80 |
| 031A (40/1) | 1.79 | 1.56 | 2.89 | 409.78 | 3.08 | 1.01 | 0.81 |
| 031B (40/3) | 1.97 | 1.99 | 3.75 | 402.32 | 3.01 | 0.96 | 0.84 |
| 031C (40/6) | 2.01 | 2.45 | 4.96 | 386.81 | 2.96 | 0.95 | 0.78 |

TABLE 38

Batch no. 032 stability, 200 mg SAMe/tbl tablets (EX. 9)

| Batch (T/t)[1] | K.F. | AD | MTAD | SAMe | SG |
|---|---|---|---|---|---|
| 032 (20/0) | 1.11 | 0.27 | 1.42 | 210.23 | 503.16 |
| 032A (40/1) | 1.21 | 0.69 | 2.15 | 208.56 | 506.01 |
| 032B (40/3) | 1.36 | 1.53 | 3.89 | 202.37 | 504.56 |
| 032C (40/6) | 1.19 | 2.56 | 4.12 | 188.59 | 502.89 |

TABLE 39

Batch no. 033- 200 mg SAMe/tbl tablets (EX. 9)

| Batch (T/t)[1] | K.F. | AD | MTAD | SAMe | SG |
|---|---|---|---|---|---|
| 033 (20/0) | 1.24 | 0.59 | 1.36 | 212.26 | 504.52 |
| 033A (40/1) | 1.32 | 0.96 | 2.66 | 207.59 | 506.74 |
| 033B (40/3) | 1.21 | 1.56 | 3.89 | 193.73 | 504.16 |
| 033C (40/6) | 1.19 | 2.59 | 5.03 | 190.47 | 500.11 |

TABLE 40

Batch 034- 200 mg SAMe/tbl tablets (EX. 9)

| Batch (T/t)[1] | K.F. | AD | MTAD | SAMe | SG |
|---|---|---|---|---|---|
| 034 (20/0) | 1.16 | 0.74 | 1.32 | 220.22 | 501.12 |
| 034A (40/1) | 1.47 | 1.51 | 2.78 | 212.43 | 507.55 |
| 034B (40/3) | 1.01 | 1.83 | 3.75 | 204.24 | 509.56 |
| 034C (40/6) | 1.27 | 2.82 | 4.37 | 198.26 | 503.44 |

TABLE 41

Batch no. 035 stability, 200 mg SAMe/tbl tablets (EX. 11)

| Batch (T/t)[1] | K.F. | AD | MTAD | SAMe | MSM. |
|---|---|---|---|---|---|
| 035 (20/0) | 1.27 | 0.34 | 1.65 | 208.54 | 500.44 |
| 035A (40/1) | 1.39 | 1.11 | 2.45 | 207.12 | 508.42 |
| 035B (40/3) | 1.46 | 1.53 | 3.24 | 198.55 | 501.22 |
| 035C (40/6) | 1.05 | 2.28 | 4.75 | 189.44 | 489.82 |

TABLE 42

Batch no. 036- 200 mg SAMe/tbl tablets (EX. 11)

| Batch (T/t)[1] | K.F. | AD | MTAD | SAMe | MSM |
|---|---|---|---|---|---|
| 036 (20/0) | 1.20 | 0.77 | 1.44 | 213.43 | 501.47 |
| 035A (40/1) | 1.17 | 1.45 | 2.57 | 209.33 | 502.91 |
| 036B (40/3) | 1.57 | 1.83 | 3.46 | 202.36 | 500.11 |
| 036C (40/6) | 1.28 | 2.60 | 4.27 | 194.10 | 492.00 |

TABLE 43

Batch no. 037- 200 mg SAMe/tbl tablets (EX. 11)

| Batch (T/t)[1] | K.F. | AD | MTAD | SAMe | MSM |
|---|---|---|---|---|---|
| 037 (20/0) | 1.42 | 0.44 | 1.54 | 211.81 | 502.57 |
| 037A (40/1) | 1.54 | 1.01 | 2.00 | 208.37 | 507.54 |
| 037B (40/3) | 1.30 | 1.27 | 3.01 | 201.16 | 505.22 |
| 037C (40/6) | 1.55 | 1.89 | 3.79 | 197.73 | 501.10 |

TABLE 44

Batch no. 038 stability, 200 mg SAMe/tbl tablets (EX. 13)

| Batch (T/t)[1] | K.F. | AD | MTAD | SAMe | SC |
|---|---|---|---|---|---|
| 038 (20/0) | 2.19 | 0.54 | 1.56 | 212.42 | 403.36 |
| 038 (40/1) | 2.05 | 1.65 | 2.89 | 204.67 | 402.98 |
| 038B (40/3) | 2.12 | 1.96 | 3.37 | 200.21 | 400.75 |
| 038C (40/6) | 1.93 | 2.67 | 4.92 | 193.87 | 397.64 |

TABLE 45

Batch no. 039- 200 mg SAMe/tbl tablets (EX. 13)

| Batch (T/t)[1] | K.F. | AD | MTAD | SAMe | SC |
|---|---|---|---|---|---|
| 039 (20/0) | 2.01 | 0.47 | 1.02 | 209.55 | 402.42 |
| 039 (40/1) | 2.27 | 1.05 | 2.32 | 204.65 | 399.37 |
| 039B (40/3) | 2.32 | 1.83 | 4.14 | 196.44 | 397.97 |
| 039C (40/6) | 2.12 | 2.71 | 5.34 | 189.81 | 398.71 |

TABLE 46

Batch no. 040- 200 mg SAMe/tbl tablets (EX. 13)

| Batch (T/t)[1] | K.F. | AD | MTAD | SAMe | SC |
|---|---|---|---|---|---|
| 040 (20/0) | 2.21 | 0.24 | 1.23 | 217.37 | 402.91 |
| 040 (40/1) | 1.87 | 1.15 | 1.74 | 214.28 | 399.39 |
| 040B (40/3) | 2.04 | 1.37 | 2.69 | 205.19 | 401.26 |
| 040C (40/6) | 2.17 | 2.02 | 3.18 | 201.73 | 391.94 |

TABLE 47

Batch no. 041 stability, 200 mg SAMe/tbl tablets (EX. 15)

| Batch (T/t)[1] | K.F. | AD | MTAD | SAMe | MSM | SC |
|---|---|---|---|---|---|---|
| 041 (20/0) | 1.88 | 0.51 | 1.71 | 205.15 | 503.32 | 402.56 |
| 041A (40/1) | 2.02 | 0.97 | 2.58 | 200.67 | 504.54 | 401.84 |
| 041B (40/3) | 1.85 | 1.42 | 3.42 | 194.34 | 503.18 | 399.11 |
| 041C (40/6) | 2.04 | 1.97 | 4.31 | 190.41 | 504.74 | 397.41 |

TABLE 48

Batch no. 042 - 200 mg SAMe/tbl tablets (EX. 15)

| Batch (T/t)[1] | K.F. | AD | MTAD | SAMe | MSM | SC |
|---|---|---|---|---|---|---|
| 042 (20/0) | 1.72 | 0.45 | 1.64 | 223.54 | 502.64 | 404.35 |
| 042A (40/1) | 1.97 | 0.93 | 2.25 | 217.96 | 507.55 | 401.42 |
| 042B (40/3) | 1.96 | 1.44 | 3.34 | 211.14 | 498.43 | 400.36 |
| 042C (40/6) | 2.16 | 2.13 | 4.03 | 204.37 | 494.41 | 402.33 |

TABLE 49

Batch no. 043 - 200 mg SAMe/tbl tablets (EX. 15)

| Batch (T/t)[1] | K.F. | AD | MTAD | SAMe | MSM | SC |
|---|---|---|---|---|---|---|
| 043 (20/0) | 1.97 | 0.35 | 1.43 | 213.28 | 503.56 | 402.73 |
| 043A (40/1) | 1.94 | 1.02 | 2.56 | 206.55 | 496.94 | 403.65 |
| 043B (40/3) | 1.86 | 1.52 | 3.36 | 202.43 | 498.67 | 403.85 |
| 043C (40/6) | 2.04 | 2.32 | 4.23 | 195.68 | 494.47 | 401.19 |

By the stability data obtained at 40° C. and 75% R.H. (stress test), it can be noted that all batches tested showed after six months a degradation lower than 10% both for SAMe and for the other active ingredients.

Comparative Stress Tests

The following tables show the stress test results, at 40° C. and 75% R.H. during a period of three months, carried out on two batches of tablets prepared according to the example no. 3, and the results of the stress test carried out on the same tablets after exposing them, for a period of 7 days, at 40° C. and 50% R.H. The samples were kept, over the three month-testing period, into closed and sealed glass bottles in order to simulate the final packaging into aluminium blisters.

TABLE 50

Batch no. 017- 200 mg SAMe/tbl tablets, protected by Biogapress ® vegetal and Labrafac ® cc.

| Batch (T/t)[1] | K.F. | AD | MTAD | SAMe |
|---|---|---|---|---|
| 03179 (20/0) | 2.11 | 0.34 | 1.56 | 216.22 |
| 03179A (40/1) | 2.18 | 1.55 | 2.89 | 213.43 |
| 017B (40/3) | 2.08 | 1.63 | 5.45 | 199.16 |

TABLE 51

(comparison)
Batch no. 018- 200 mg SAMe/tbl tablets, without the protection of Biogapress ® vegetal and Labrafac ® cc, but desiccated before undergoing gastroresistant film coating.

| Batch (T/t)[1] | K.F. | AD | MTAD | SAMe |
|---|---|---|---|---|
| 03181 (20/0) | 1.65 | 0.29 | 1.83 | 211.20 |
| 03179A (40/1) | 1.95 | 1.04 | 2.55 | 202.30 |
| 017B (40/3) | 1.77 | 1.88 | 3.36 | 196.25 |

TABLE 52

Batch no. 017- 200 mg SAMe/tbl tablets, protected by Biogapress ® vegetal and Labrafac ® cc and exposed to 40° C. and 50% R.H.

| Batch (T/t)[1] | K.F. | AD | MTAD | SAMe |
|---|---|---|---|---|
| 03179 (20/0) | 2.11 | 0.34 | 1.56 | 216.22 |
| 03179A (40/1) | 2.79 | 1.95 | 3.09 | 200.23 |
| 0317B (40/3) | 2.81 | 4.04 | 6.51 | 180.63 |

TABLE 53

(comparison)
Batch no. 018- 200 mg SAMe/tbl tablets, without Biogapress ® vegetal and Labrafac ® cc protection, desiccated before undergoing gastro-resistant film coating and exposed at 40° C. and 50% R.H. for 7 days.

| Batch (T/t)[1] | K.F. | AD | MTAD | SAMe |
|---|---|---|---|---|
| 03181 (20/0) | 1.65 | 0.29 | 1.83 | 211.20 |
| 018A (40/1) | 4.85 | 7.04 | 4.15 | 166.63 |
| 03181B (40/3) | 4.62 | 18.85 | 6.98 | 118.72 |

The results showed in the latest four tables, as those ones shown in the previous tables relating to the stress test show the high stability and the low hygroscopicity of the tablets obtainable by the process of the invention.

As a further confirmation of the results obtainable by carrying out the invention, the product Samyr® (Knoll) 200 mg SAMe/tbl tablets—batch no. 125—was bought to comparatively evaluate it against a sample of the tablets obtainable by the process of the invention (batch 017—200 mg SAMe/tbl tablets coated by Biogapress® vegetal and Labrafac®cc, example 3); both batches were exposed at a temperature of 40° C. and at 75% R.H., for 7 days.

TABLE 54

| Batch (T/t) | K.F. | AD | MTAD | SAMe |
|---|---|---|---|---|
| 03179 (20/) | 2.01 | 0.37 | 1.54 | 210.15 |
| 03179A (55/3) | 2.39 | 1.85 | 2.89 | 201.25 |
| 03181B (55/7) | 2.79 | 4.15 | 5.81 | 182.75 |

TABLE 55

(comparison)

| Batch (T/t) | K.F. | AD | MTAD | SAMe |
|---|---|---|---|---|
| 125 (20/) | 1.75 | 0.34 | 1.12 | 209.12 |
| 125A (55/3) | 3.01 | 6.48 | 4.41 | 176.15 |
| 125B (55/7) | 4.77 | 17.41 | 7.14 | 129.42 |

According to the data in the latest two tables, it can be noted that the tablets obtainable by the process of the invention show a humidity increase four times lower and are, therefore, four times less hygroscopic than the commercialised tablets used for the comparison; the tablets obtainable by the process of the invention result therefore to be more stable (for example, the AD amount at a temperature of 55° C. after 7 days, is more than four times higher in the case of Samyr® than the tablets of the invention) even after accidental exposures to environmental humidity, due, for example, to microfractures of the aluminium blisters wherein the tablets are usually packed.

Shelf Life

The tablets were packed in closed and sealed glass bottles so as to simulate the final packaging conditions (generally, in aluminium blisters).

The samples were selected according to the same method and amounts described for the stress test and preserved in a thermostated environment at a temperature of 25±2° C. and at 60% R.H.

Nine samples from three different batches were used for the 200 mg tablets (Ex. 3, 9, 11, 13, 15) and further nine samples from three different batches were used for the 400 mg tablets (Ex. 1, 5, 7) wherein each sample, of every single batch, was sampled after 0, 3, 6, 12, 24 and 36 months.

TABLE 56

Batch no. 023- 400 mg SAMe/tbl tablets (EX. 1)

| Batch (T/t) | K.F. | AD | MTAD | SAMe |
|---|---|---|---|---|
| 023 (20/0) | 1.78 | 0.31 | 1.16 | 422.42 |
| 023A (25/3) | 1.79 | 0.42 | 1.11 | 423.85 |
| 023B (25/6) | 1.82 | 0.56 | 1.23 | 129.42 |
| 023C (25/12) | 1.82 | 0.55 | 1.57 | 416.32 |

TABLE 57

Batch no. 024- 400 mg SAMe/tbl tablets (EX. 1)

| Batch (T/t) | K.F. | AD | MTAD | SAMe |
|---|---|---|---|---|
| 024 (20/0) | 1.86 | 0.31 | 1.27 | 423.93 |
| 024A (25/3) | 1.72 | 0.39 | 1.25 | 420.56 |
| 024B (25/6) | 1.65 | 0.49 | 1.44 | 421.76 |
| 024C (25/12) | 1.87 | 0.75 | 1.69 | 414.34 |

TABLE 58

Batch no. 025- 400 mg SAMe/tbl tablets (EX. 1)

| Batch (T/t) | K.F. | AD | MTAD | SAMe |
|---|---|---|---|---|
| 025 (20/0) | 1.70 | 0.47 | 1.42 | 423.51 |
| 025A (25/3) | 1.87 | 0.58 | 1.49 | 416.45 |
| 025B (25/6) | 2.09 | 0.94 | 1.62 | 419.91 |
| 025C (25/12) | 1.93 | 1.02 | 1.77 | 415.37 |

TABLE 59

Batch no. 015- 200 mg SAMe/tbl tablets (EX. 3)

| Batch (T/t)[1] | K.F. | AD | MTAD | SAMe |
|---|---|---|---|---|
| 015 (20/0) | 1.89 | 0.42 | 2.08 | 240.60 |
| 015A (25/3) | 1.75 | 0.51 | 2.05 | 233.19 |
| 015B (25/6) | 2.01 | 0.55 | 1.95 | 218.62 |
| 015C (25/12) | 1.82 | 0.64 | 2.41 | 227.51 |

TABLE 60

Batch no. 017- 200 mg SAMe/tbl tablets (EX. 3)

| Batch (T/t)[1] | K.F. | AD | MTAD | SAMe |
|---|---|---|---|---|
| 017 (20/0) | 2.11 | 0.34 | 1.56 | 216.22 |
| 017A (25/3) | 1.82 | 0.29 | 1.69 | 217.83 |
| 017B (25/6) | 1.79 | 0.38 | 1.68 | 215.46 |
| 017C (25/12) | 1.86 | 0.49 | 1.77 | 211.12 |

TABLE 61

Batch no. 018, 200 mg SAMe/tbl tablets (EX. 3)

| Batch (T/t)[1] | K.F. | AD | MTAD | SAMe |
|---|---|---|---|---|
| 018 (20/0) | 1.65 | 0.29 | 1.83 | 211.20 |
| 018A (25/3) | 1.55 | 0.24 | 2.05 | 212.00 |
| 018B (25/6) | 1.83 | 0.37 | 2.12 | 208.67 |
| 018C (25/12) | 1.94 | 0.75 | 2.16 | 204.22 |

TABLE 62

Batch no. 026, 600 mg SAMe/tbl tablets (EX. 5)

| Batch (T/t)[1] | K.F. | AD | MTAD | SAMe | V.B$_6$ | V.B$_{12}$ | FA |
|---|---|---|---|---|---|---|---|
| 026 (20/0) | 2.22 | 0.39 | 1.22 | 630.56 | 3.07 | 1.03 | 0.83 |
| 026A (25/3) | 1.95 | 0.38 | 1.37 | 627.95 | 3.05 | 1.06 | 0.82 |
| 026B (25/6) | 2.03 | 0.57 | 1.51 | 621.15 | 2.98 | 1.01 | 0.82 |
| 026C (25/12) | 1.83 | 0.85 | 1.69 | 615.37 | 2.86 | 0.98 | 0.78 |

TABLE 63

Batch no. 027, 600 mg SAMe/tbl tablets (EX. 5)

| Batch (T/t)[1] | K.F. | AD | MTAD | SAMe | V.B$_6$ | V.B$_{12}$ | FA |
|---|---|---|---|---|---|---|---|
| 027 (20/0) | 1.58 | 0.55 | 1.57 | 627.67 | 3.10 | 1.10 | 0.89 |
| 027A (25/3) | 1.66 | 0.49 | 1.65 | 620.63 | 2.95 | 1.07 | 0.80 |
| 027B (25/6) | 1.73 | 0.59 | 1.64 | 608.71 | 3.03 | 1.06 | 0.84 |
| 027C (25/12) | 1.78 | 0.64 | 1.84 | 603.52 | 3.02 | 1.03 | 0.83 |

TABELLA 64

Batch no. 028, 600 mg SAMe/tbl tablets (EX. 5)

| Batch (T/t)[1] | K.F. | AD | MTAD | SAMe | V.B$_6$ | V.B$_{12}$ | FA |
|---|---|---|---|---|---|---|---|
| 028 (20/0) | 2.05 | 0.44 | 1.28 | 635.88 | 3.03 | 1.02 | 0.80 |
| 028A (25/3) | 1.96 | 0.57 | 1.33 | 627.26 | 2.87 | 1.00 | 0.81 |
| 028B (25/6) | 1.77 | 0.63 | 1.37 | 620.21 | 2.96 | 0.96 | 0.80 |
| 028C (25/12) | 2.02 | 1.02 | 1.79 | 613.34 | 2.90 | 0.96 | 0.78 |

TABLE 65

Batch 029 - 400 mg SAMe/tbl tablets (EX. 7)

| Batch (T/t)[1] | K.F. | AD | MTAD | SAMe | V.B$_6$ | V.B$_{12}$ | FA |
|---|---|---|---|---|---|---|---|
| 029 (20/0) | 1.95 | 0.31 | 1.42 | 415.91 | 3.01 | 1.02 | 0.82 |
| 029A (25/3) | 1.99 | 0.52 | 1.58 | 416.76 | 3.00 | 0.98 | 0.83 |
| 029B (25/6) | 1.78 | 0.47 | 1.67 | 413.45 | 2.97 | 1.01 | 0.82 |
| 029C (25/12) | 2.01 | 0.84 | 1.79 | 403.11 | 2.88 | 0.99 | 0.78 |

TABELLA 66

Batch no. 030, 400 mg SAMe/tbl tablets (EX. 7)

| Batch (T/t)[1] | K.F. | AD | MTAD | SAMe | V.B$_6$ | V.B$_{12}$ | FA |
|---|---|---|---|---|---|---|---|
| 030 (20/0) | 2.05 | 0.55 | 1.59 | 421.01 | 3.11 | 1.01 | 0.79 |
| 030A (25/3) | 2.02 | 0.56 | 1.96 | 418.37 | 3.03 | 0.98 | 0.80 |
| 030B (25/6) | 1.89 | 0.75 | 1.88 | 419.11 | 3.05 | 1.03 | 0.78 |
| 030C (25/12) | 2.09 | 0.98 | 1.95 | 408.33 | 2.97 | 0.98 | 0.78 |

TABELLA 67

Batch no. 031, 400 mg SAMe/tbl tablets (EX. 7)

| Batch (T/t)[1] | K.F. | AD | MTAD | SAMe | V.B$_6$ | V.B$_{12}$ | FA |
|---|---|---|---|---|---|---|---|
| 031 (20/0) | 1.87 | 0.47 | 1.72 | 417.56 | 3.12 | 1.04 | 0.80 |
| 031A (25/3) | 1.79 | 0.50 | 1.89 | 419.00 | 3.03 | 1.02 | 0.79 |
| 031B (25/6) | 1.83 | 0.69 | 1.95 | 413.23 | 3.04 | 0.97 | 0.82 |
| 031C (25/12) | 1.68 | 0.88 | 2.16 | 402.18 | 3.01 | 0.97 | 0.77 |

TABLE 68

Batch no. 032- 200 mg SAMe/tbl tablets (EX. 9)

| Batch (T/t)[1] | K.F. | AD | MTAD | SAMe | SG |
|---|---|---|---|---|---|
| 032 (20/0) | 1.11 | 0.27 | 1.42 | 210.23 | 503.16 |
| 032A (25/3) | 0.96 | 0.38 | 1.38 | 212.00 | 502.01 |
| 032B (25/6) | 1.12 | 0.69 | 1.86 | 207.11 | 503.56 |
| 032C (25/12) | 1.29 | 0.87 | 2.03 | 205.19 | 499.89 |

TABLE 69

Batch no. 033, 200 mg SAMe/tbl tablets (EX. 9)

| Batch (T/t)[1] | K.F. | AD | MTAD | SAMe | SG |
|---|---|---|---|---|---|
| 033 (20/0) | 1.24 | 0.59 | 1.36 | 212.26 | 504.52 |
| 033A (25/3) | 1.02 | 0.56 | 1.43 | 209.54 | 501.47 |
| 033B (25/6) | 1.21 | 0.76 | 1.68 | 210.26 | 500.76 |
| 033C (25/12) | 1.33 | 1.09 | 1.83 | 208.73 | 496.17 |

TABLE 70

Batch no. 034, 200 mg SAMe/tbl tablets (EX. 9)

| Batch (T/t)[1] | K.F. | AD | MTAD | SAMe | SG |
|---|---|---|---|---|---|
| 034 (20/0) | 1.16 | 0.74 | 1.32 | 220.22 | 501.12 |
| 034A (25/3) | 1.23 | 0.81 | 1.28 | 218.35 | 498.33 |
| 034B (25/6) | 1.08 | 0.83 | 1.35 | 219.73 | 499.16 |
| 034C (25/12) | 1.17 | 0.98 | 1.67 | 216.13 | 496.83 |

TABLE 71

Batch no. 035, 200 mg SAMe/tbl tablets (EX. 9)

| Batch (T/t)[1] | K.F. | AD | MTAD | SAMe | MSM |
|---|---|---|---|---|---|
| 035 (20/0) | 1.27 | 0.34 | 1.65 | 208.54 | 505.44 |
| 035A (25/3) | 1.33 | 0.41 | 1.87 | 210.17 | 501.26 |
| 035B (25/6) | 1.26 | 0.63 | 1.97 | 206.76 | 502.16 |
| 035C (25/12) | 1.05 | 0.84 | 2.15 | 202.44 | 497.87 |

TABLE 72

Batch no. 036, 200 mg SAMe/tbl tablets (EX. 11)

| Batch (T/t)[1] | K.F. | AD | MTAD | SAMe | MSM |
|---|---|---|---|---|---|
| 036 (20/0) | 1.20 | 0.77 | 1.44 | 213.43 | 501.4 |
| 036A (25/3) | 1.35 | 0.85 | 1.57 | 209.73 | 501.19 |
| 036B (25/6) | 1.13 | 0.97 | 1.76 | 211.12 | 496.71 |
| 036C (25/12) | 1.24 | 1.02 | 1.97 | 206.34 | 497.05 |

TABLE 73

Batch no. 037, 200 mg SAMe/tbl tablets (EX. 11)

| Batch (T/t)[1] | K.F. | AD | MTAD | SAMe | MSM |
|---|---|---|---|---|---|
| 037 (20/0) | 1.42 | 0.44 | 1.54 | 211.81 | 502.57 |
| 037A (25/3) | 1.27 | 0.68 | 1.86 | 209.44 | 498.14 |
| 037B (25/6) | 1.30 | 1.01 | 2.01 | 205.16 | 500.76 |
| 037C (25/12) | 1.52 | 1.09 | 2.39 | 201.53 | 497.12 |

TABLE 74

Batch 038- 200 mg SAMe/tbl tablets (EX. 13)

| Batch (T/t)[1] | K.F. | AD | MTAD | SAMe | SC |
|---|---|---|---|---|---|
| 038 (20/0) | 2.19 | 0.54 | 1.56 | 212.42 | 403.36 |
| 038A (25/3) | 2.03 | 0.49 | 1.59 | 212.56 | 401.42 |
| 038B (25/6) | 2.23 | 0.63 | 1.71 | 211.89 | 401.18 |
| 038C (25/12) | 2.30 | 0.84 | 1.82 | 208.13 | 398.74 |

TABLE 75

Batch no. 039- 200 mg SAMe/tbl tablets (EX. 13)

| Batch (T/t)[1] | K.F. | AD | MTAD | SAMe | SC |
|---|---|---|---|---|---|
| 039 (20/0) | 2.01 | 0.47 | 1.02 | 209.55 | 402.42 |
| 039A (25/1) | 2.15 | 0.55 | 1.32 | 210.39 | 401.37 |
| 039B (25/3) | 1.92 | 0.73 | 1.43 | 208.14 | 398.79 |
| 039C (25/6) | 2.14 | 0.91 | 1.84 | 205.93 | 396.17 |

TABLE 76

Batch no. 040, 200 mg SAMe/tbl tablets (EX. 13)

| Batch (T/t)[1] | K.F. | AD | MTAD | SAMe | SC |
|---|---|---|---|---|---|
| 040 (20/0) | 2.21 | 0.24 | 1.23 | 217.37 | 402.91 |
| 040A (25/3) | 1.88 | 0.33 | 1.37 | 216.73 | 401.10 |
| 040B (25/6) | 2.03 | 0.57 | 1.49 | 213.14 | 398.26 |
| 040C (25/12) | 2.11 | 0.82 | 1.68 | 214.95 | 394.72 |

TABLE 77

Batch no. 041 - 200 mg SAMe/tbl tablets (EX. 15)

| Batch (T/t)[1] | K.F. | AD | MTAD | SAMe | MSM | SC |
|---|---|---|---|---|---|---|
| 041 (20/0) | 1.88 | 0.51 | 1.71 | 205.15 | 503.32 | 402.56 |
| 041A (25/3) | 1.92 | 0.63 | 1.88 | 206.32 | 502.84 | 400.71 |
| 041B (25/6) | 1.85 | 0.69 | 1.79 | 204.76 | 499.18 | 398.42 |
| 041C (25/12) | 2.04 | 0.72 | 1.93 | 200.54 | 496.84 | 399.70 |

TABLE 78

Batch 042 - 200 mg SAMe/tbl tablets (EX. 15)

| Batch (T/t)[1] | K.F. | AD | MTAD | SAMe | MSM | SC |
|---|---|---|---|---|---|---|
| 042 (20/0) | 1.72 | 0.45 | 1.64 | 223.54 | 502.64 | 404.35 |
| 042A (25/3) | 1.76 | 0.39 | 1.77 | 221.99 | 500.52 | 389.32 |
| 042B (25/6) | 1.87 | 0.66 | 1.93 | 216.19 | 498.98 | 400.36 |
| 042C (25/12) | 1.83 | 0.95 | 2.07 | 217.31 | 496.32 | 393.40 |

TABLE 79

Batch no. 043, 200 mg SAMe/tbl tablets (EX. 15)

| Batch (T/t)[1] | K.F. | AD | MTAD | SAMe | MSM | SC |
|---|---|---|---|---|---|---|
| 043 (20/0) | 1.97 | 0.35 | 1.43 | 213.28 | 503.56 | 402.73 |
| 043A (25/3) | 1.81 | 0.47 | 1.49 | 209.39 | 500.04 | 401.99 |
| 043B (25/6) | 1.65 | 0.50 | 1.61 | 210.34 | 496.22 | 397.43 |
| 043C (25/12) | 1.79 | 0.87 | 1.95 | 207.68 | 495.74 | 397.91 |

According to the stability data at 25° C. and 60% R.H. (shelf life), it can be noted that in all of the batches tested after 12 months, both SAMe and the other active ingredients had undergone a very low degradation.

What is claimed is:

1. A process for the preparation of tablets comprising S-adenosylmethionine and/or a pharmaceutically and/or dietarily acceptable salt thereof, comprising at a relative humidity, at 20° C., lower or equal to 20%, the following steps:
   a) blending of said S-adenosylmethionine and/or a pharmaceutically and/or dietarily acceptable salt thereof with 1.0–30.0% of calcium sulfate and/or phosphate, 1.0–10.0% of calcium and/or magnesium carbonate, 1.0–15.0% of glycerol behenate and/or palmitostearate and 0.5–5.0% of silica, the amounts being expressed as weight percentages to the weight of said S-adenosylmethionine and/or a pharmaceutically and/or dietarily acceptable salt thereof;
   b) compressing the blend resulting from step a);
   c) coating the blend resulting from step b) by 0.5–2.5% of glycerol palmitostearate and 0.5–2.5% of caprylic/capric triglyceride, at a temperature of 35° C.–45° C., after 10 to 30 minutes at 60° C.–65° C., the quantities being expressed as weight percentages to the total weight of the blend resulting from step b).

2. The process of claim 1, further comprising, after blending step a):
   a') pre-compressing the blend resulting from step a); and
   a") granulating the blend resulting from step a').

3. The process of claim 1, wherein said S-adenosylmethionine and/or a pharmaceutically and/or dietarily acceptable salt thereof is selected from the group consisting of the salts with sulfuric acid and/or paratoluensulfonic acid.

4. The process of claim 1, wherein, in step a), 1.0–30.0% by weight, based on the weight of said S-adenosylmethionine and/or a pharmaceutically and/or dietarily acceptable salt thereof, of anhydrous microcrystalline cellulose is added.

5. The process of claim 1, further comprising coating the tablets with a gastroresistant film.

6. The process of claim 5, wherein the gastroresistant film comprises 1.0–5.0% of acrylate/methacrylate copolymer and/or resin obtained from the Lac insect and/or at least a water-soluble salt of resin obtained from the Lac insect, 1.0–3.0% of titanium dioxide, 1.0–3.0% of talc, 0.1%–1.0% of triethylcitrate and/or glycerine, 0.004–0.04% of ferric oxide, the amounts being expressed as weight percentages to the total weight of the blend resulting from step b).

7. The process of claim 5, wherein the gastroresistant film comprises 1.0–5.0% of resin obtained from the Lac insect and/or at least a water-soluble salt of resin obtained from the Lac insect, 1.0–3.0% of titanium dioxide, 1.0–3.0% of talc, 0.1–1.0% of triethylcitrate, 0.004–0.04% of ferric oxide, the amounts being expressed as weight percentages to the total weight of the blend resulting from step b).

8. The process of claim 5, wherein the gastroresistant film comprises 1.0–5.0% of at least one water-soluble salt of resin obtained from the Lac insect.

9. The process of claim 5, wherein the gastroresistant film comprises 1.0–5.0% of a 1:1 mixture of the potassium and ammonium salts of resin obtained from the Lac insect.

10. The process of claim 1, wherein, in step a), at least one further active ingredient is added.

11. The process of claim 10, wherein said further active ingredient is selected from the group consisting of 100–150% of glucosamine sulfate, 80–120% of chondroitin sulfate, 100–150% of methylsulfonylmethane, 0.1–0.5% of vitamin $B_6$, 0.04–0.2% of vitamin $B_{12}$, 0.03–0.15% of folic acid, the amounts being expressed as weight percentages to the weight of said S-adenosylmethionine and/or a pharmaceutically and/or dietarily acceptable salt thereof.

12. The process of claim 1, wherein said S-adenosylmethionine and/or a pharmaceutically and/or dietarily acceptable salt thereof is S-adenosylmethionine.

13. The process of claim 1, wherein said S-adenosylmethionine and/or a pharmaceutically and/or dietarily acceptable salt thereof is a pharmaceutically acceptable derivative of S-adenosylmethionine.

14. The process of claim 1, wherein said S-adenosylmethionine and/or a pharmaceutically and/or dietarily acceptable derivative thereof is a salt of S-adenosylmethionine.

* * * * *